(12) United States Patent
Mao et al.

(10) Patent No.: US 7,507,469 B2
(45) Date of Patent: *Mar. 24, 2009

(54) MULTI-LAYER COATED POROUS MATERIALS AND METHODS OF MAKING THE SAME

(75) Inventors: Guoqiang Mao, Smyrna, GA (US); George Greene, IV, Peachtree City, GA (US); Li Yao, Peachtree City, GA (US)

(73) Assignee: Porex Corporation, Fairburn, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/506,353

(22) Filed: Aug. 18, 2006

(65) Prior Publication Data

US 2006/0280931 A1    Dec. 14, 2006

Related U.S. Application Data

(63) Continuation of application No. 10/228,944, filed on Aug. 28, 2002, now Pat. No. 7,094,464.

(60) Provisional application No. 60/315,043, filed on Aug. 28, 2001, provisional application No. 60/315,044, filed on Aug. 28, 2001.

(51) Int. Cl.
*B32B 27/08* (2006.01)
(52) U.S. Cl. .............. 428/319.3; 428/319.7; 428/319.9; 436/518; 436/169; 436/164; 422/56; 422/57; 422/68.1; 73/864.72
(58) Field of Classification Search .............. 428/319.3, 428/319.7, 319.9; 436/169, 164; 422/56, 422/57, 68.1; 73/864.72
See application file for complete search history.

(56) References Cited

U.S. PATENT DOCUMENTS

| 4,250,029 A | 2/1981 | Kiser et al. |
| 4,519,909 A | 5/1985 | Castro |
| 4,560,599 A | 12/1985 | Regen |
| 4,619,897 A | 10/1986 | Hato et al. |
| 4,683,196 A | 7/1987 | McLaughlin |
| 4,845,132 A | 7/1989 | Masuoka et al. |

(Continued)

FOREIGN PATENT DOCUMENTS

EP    0 099 432    7/1982

(Continued)

OTHER PUBLICATIONS

Supplemental European Search Report dated Nov. 12, 2004.

(Continued)

*Primary Examiner*—Hai Vo
(74) *Attorney, Agent, or Firm*—J. Clinton Wimbish; John K. McDonald; Kilpatrick Stockton LLP

(57) ABSTRACT

Multi-layer coated materials and methods of making them are disclosed. In a specific embodiment, a porous polymeric substrate is pre-activated and immersed in a polyelectrolyte solution to form a first layer having an electric charge and at least one functional group. The coated material is next immersed in a second solution of a material having an electric charge opposite of that of the first layer to provide a bi-layer coating. This process can be repeated to form multi-layer coatings on porous substrates.

9 Claims, 8 Drawing Sheets

U.S. PATENT DOCUMENTS

| | | |
|---|---|---|
| 4,859,538 A | 8/1989 | Ribi |
| 4,943,522 A | 7/1990 | Eisinger et al. |
| 4,944,879 A | 7/1990 | Steuck |
| 5,064,541 A | 11/1991 | Jeng et al. |
| 5,224,972 A | 7/1993 | Frye et al. |
| 5,540,837 A | 7/1996 | Lunkwitz et al. |
| 5,695,640 A | 12/1997 | Tseng |
| 5,700,559 A | 12/1997 | Sheu et al. |
| 5,748,438 A | 5/1998 | Davis et al. |
| 5,807,636 A | 9/1998 | Sheu et al. |
| 5,837,377 A | 11/1998 | Sheu et al. |
| 5,856,246 A | 1/1999 | Witzko et al. |
| 5,914,182 A | 6/1999 | Drumheller |
| 5,916,585 A | 6/1999 | Cook et al. |
| 5,998,588 A | 12/1999 | Hoffman et al. |
| 6,020,175 A | 2/2000 | Onda et al. |
| 6,060,410 A | 5/2000 | Gillberg-LaForce et al. |
| 6,107,084 A | 8/2000 | Onda et al. |
| 6,486,245 B1 | 11/2002 | Thunemann et al. |
| 6,638,760 B1 | 10/2003 | Chen et al. |
| 6,808,908 B2 | 10/2004 | Yao et al. |
| 2002/0039648 A1 | 4/2002 | Horpel et al. |
| 2003/0008413 A1 | 1/2003 | Kim et al. |
| 2003/0096424 A1 | 5/2003 | Mao et al. |

FOREIGN PATENT DOCUMENTS

| | | |
|---|---|---|
| EP | 0 153 133 | 12/1991 |
| EP | 0 941 739 | 9/1999 |

OTHER PUBLICATIONS

Van Ackern et al., "Ultrathin membranes for gas separation and pervaporation prepared upon electrostatic self-assembly of polyelectrolytes," *Thin Solid Films*, 1998, 327-329:762-766.

Krasemann et al., "Self-assembled polyelectrolyte multilayer membranes with highly improved pervaporation separation of ethanol/water mixtures," *J. Membrane Sci.*, 2001, 181:221-228.

Bsiesy et al., "Electroluminescence from n+-type porous silicon contacted with layer-by-layer deposited polyaniline," *Thin Solid Films*, 1995, 225:43-48.

Onda et al., "Sequential Actions of Glucose Oxidase and Peroxidase in Molecular Films Assembled by Layer-by-Layer Alternate Adsorption," *Biotechnology and Bioengineering*, 1996, 51:163-167.

Lvov, et al., "Assembly of Multicomponent Protein Films by Means of Electrostatic Layer-by-Layer Adsorption," *J. Am. Chem. Soc.*, 1995, 117:6117-6123.

U.S. Appl. No. 10/158,881 Notice of Allowance and Fees Due mailed Sep. 16, 2008.

MULTI-LAYER COATED POROUS MATERIALS AND METHODS OF MAKING THE SAME

1. RELATED APPLICATIONS

The present application is a continuation of U.S. patent application Ser. No. 10/228,944, filed Aug. 28, 2002 now U.S. Pat. No. 7,094,464, which claims priority to U.S. provisional patent application Nos. 60/315,043 and 60/315,044, both filed on Aug. 28, 2001, the contents of which are incorporated by reference.

2. FIELD OF THE INVENTION

This application is directed, in part, to multi-layer coated substrates, preferably porous polymeric substrates, wherein the coating is made up of at least two layers, and to methods of making the same.

3. BACKGROUND OF THE INVENTION

Porous materials, including metal, ceramic, glass and polymeric materials, have increasingly been used in a variety of applications, such as filtration, aeration, wicking, and implant and other biomedical devices. For example, porous polymeric materials can be used in medical devices that serve as substitute blood vessels, synthetic and intra-ocular lenses, electrodes, catheters, and extra-corporeal devices such as those that are connected to the body to assist in surgery or dialysis. Porous polymeric materials can also be used as filters for the separation of blood into component blood cells and plasma, microfilters for removal of microorganisms from blood, and coatings for ophthalnic lenses to prevent endothelial damage upon implantation. Porous materials have also been used in diagnostic devices such as lateral flow devices, flow through devices and other immunoassay devices.

It is often necessary to alter the surface properties of a porous material, since the application of porous materials is often limited by their lack of chemical functional group and/or their hydrophobic properties, which may be disadvantageous in applications such as liquid filtration, extraction, separation and immobilization of small molecules, polymers or large biomolecules. For example, proteins will often denature when placed in contact with hydrophobic materials, and hydrophobic porous materials cannot wick aqueous solutions. Contact lenses, implants, and related devices that are in intimate contact with the body must have hydrophilic surfaces that are biologically compatible.

Attempts have been made to modify porous materials, but with mixed success. For example, U.S. Pat. No. 4,250,029 discloses a method of manufacturing ionic rejection membrane by coating differently charged polyelectrolytes onto a membrane with a neutral polymer layer between two electrolytes. The patent, however, is directed to thin ion rejection membranes only.

U.S. Pat. No. 4,619,897 discloses that the physical and/or chemical properties of a plastic surface can be changed by adhering or bonding a different material to it.

U.S. Pat. No. 4,845,132 discloses a method that uses plasma and hydrophilic monomer to produce a hydrophilic porous membrane. However, the resulted polymer film deposited by this method is not stable; and hydrophilic monomer or polymers tend to leach out.

U.S. Pat. No. 5,540,837 discloses a method of producing permanent hydrophilic fluoropolymers by coating a charged polyelectrolyte complex on top of the fluoropolymer. The application of this patent, however, is limited to the fluorinated polymer membrane and the adhesion between the polyelectrolyte complex and fluorinated polymer substrate is poor due to the lack of strong interactions between the polyelectrolyte complex and the fluorinated membrane.

U.S. Pat. No. 5,695,640 discloses a method for producing a hydrophilic porous article by treating a porous article with the mixture of polyamide and calcium chloride methanol solution. However, the stability of the hydrophilicity obtained by this method is poor.

U.S. Pat. Nos. 5,700,559; 5,807,636 and 5,837,377 disclose a method of modifying the surfaces of plastics with plasma and sequential PEI solution treatment to provide the plastics with hydrophilicity. This method can allegedly provide relatively stable hydrophilic plastics. However, the wicking rate of the plastics deteriorates during the storage.

U.S. Pat. No. 5,856,246 discloses a method of surface modification of materials using water soluble polycation and long chain surfactant or alkyl-substituted polyanion to make fiber, textiles, polymer and membrane permanent hydrophobic or oleophobic. The method disclosed therein, however, is suitable only for charged materials, not for neutral polymers such as polyolefins.

U.S. Pat. Nos. 5,914,182 and 5,916,585 disclose a method for improving porous membrane's biomaterial binding properties by treating the porous membrane with a polymer surfactant solution. The polymeric surfactant binds to the support material through hydrophobic interactions. The first layer is then crosslinked by a chemical reagent. A secondary hydrophilic layer is brought to the membrane by dipping the membrane into a hydrophilic polymer solution. This hydrophilic polymer coating allegedly can improve biomolecule binding and form covalent bonds with the first layer. This method, however, only works on ultrathin membranes. Further, the binding between the polymer surfactant and the membrane support is weak because the binding force is based on hydrophobic interaction. In addition, the crosslinking reagent glutaldehyde used therein is highly toxic.

U.S. Pat. No. 6,020,175 discloses a method of producing multiple layered functional thin films (such as protein and dye) onto solid supports by immersing charged solid substrates into an admixed polymer ion-functional molecule solution having a net opposite electric charge. This step can be repeated to form multi-layered film. The patent is directed to solid non-porous materials.

U.S. Pat. No. 6,060,410 discloses a method of coating a hydrophobic polymer substrate with a nonstoichiometric polyelectrolyte complex in solution.

Thus, there is still a need for materials, especially porous materials, with controllable and stable wicking rates, low leaching rates, and/or functional groups that enhance the materials' application potential in filtration, separation, diagnostics and medical device areas. More specifically, there is a need to provide porous polymeric materials with controllable wicking rates, biomolecular binding abilities, chemical reactivities, and ionic selection abilities.

4. SUMMARY OF THE INVENTION

The present invention provides multi-layer coated materials and methods of making such materials. Specific methods utilize solution treatment with sequential polyelectrolyte solution.

The materials of this invention can be used in a variety of applications as filters, films, lateral flow membranes, conjugate pads, extraction materials, and blood separation materials. Materials of this invention can be produced economically and/or consistently and can exhibit one or more of the following properties: permanent hydrophilicity or hydrophobicity, high density functional groups; limited leaching; strong and/or specific binding ability to a variety of reagents such as proteins and other biomolecules; controllable and/or narrower distribution of porosities; controllable and wide wicking rates; flexible strength for different applications.

In one aspect, the present invention provides a multi-layer coated material comprising a substrate, a first layer, and a second layer. The substrate comprises a sintered porous polymeric material; the first layer comprises molecules bound to a surface of the substrate through covalent bounds, electrostatic interactions, or combinations thereof; and the second layer comprises molecules bound to the first layer through covalent bounds, electrostatic interactions, or combinations thereof.

In a specific embodiment, the polymeric material is a polyolefin, polyester, polyurethane, polycarbonate, polyetheretherketone, poly(phenylene oxide), poly(ether sulfone), or nylon. In another specific embodiment, the polyolefin is ethylene vinyl acetate, ethylene methyl acrylate, polyethylene, polypropylene, ethylene-propylene rubber, ethylene-propylene-diene rubbers, poly(1-butene), polystyrene, poly(2-butene), poly(1-pentene), poly(2-pentene), poly(3-methyl-1-pentene), poly(4-methyl-1-pentene), 1,2-poly-1,3-butadiene, 1,4-poly-1,3-butadiene; polyisoprene, polychloroprene, poly(vinyl acetate), poly(vinylidene chloride), poly(vinylidene fluoride), poly(tetra fluoro ethylene), or mixture thereof.

In one embodiment, the molecules of the first layer and the second layer of the multi-layer coated material are independently selected from polyelectrolyte, surfactant, neutral polymer, small molecule, biomolecule, or combination thereof.

Specific polyelectrolytes include, but are not limited to, phosphates, polyethyleneimides, poly(vinylimidazoline), quaterized polyacrylamides, polyvinylpyridines, poly(vinylpyrrolidone), polyvinylamines, polyallylamines, chitosans, polylysines, poly(acrylate trialkyl ammonia salt ester), cellulose, poly(acrylic acid), polymethylacrylic acid, poly(styrenesulftric acid), poly(vinylsulfonic acid), poly(toluene sulfuric acid), poly(methyl vinyl ether-alt-maleic acid), poly(glutamic acid), surfactants, dextran sulfates, hyaluric acid, heparin, alginic acid, adipic acid, chemical dyes, proteins, enzymes, nucleic acids, peptides, and a salts, esters, and copolymers thereof.

Specific neutral polymers include, but are not limited to, isocyannated terminated polymer, epoxy-terminated polymer, or hydroxylsuccimide terminated polymer. More specific examples of neutral polymer include polyurethane, poly(ethylene glycol), and polysiloxane.

Specific mall molecules include, but are not limited to, sodium dodecylsulfonate, dodecyltrimethylamonium bromide, phosphate, sulfonate, bronate, sulfonate, dye, lipid, metal ion, or surfactant containing fluorine.

Specific biomolecules include, but are not limited to, proteins, enzymes, lipids, hormones, peptidse, nucleic acids, oligonucleic acids, DNA, RNA, sugars, or polysaccharides.

In another specific embodiment of the multi-layer coated material of this invention, the first layer comprises molecules of polyethyleneimide and the second layer comprises molecules of a poly(acrylic acid), a copolymer containing poly(acrylic acid), or a surfactant, such as a fluorinated surfactant. Alternatively, the first layer comprises molecules of polyallylammoniumchloride, and the second layer comprises molecules of polyvinylsulfate.

In another embodiment, the substrate is further coated with one or more additional layers bound to the second or one of the additional layers through covalent bounds, electrostatic interactions, or combinations thereof. For example, the substrate can be coated with three layers with the first layer comprising molecules of polyethyleneimide, the second layer comprising molecules of a polyallylamine, and the third layer comprising of molecules of polyethyleneimide, polyvinylamine, or a surfactant.

Another aspect of this invention provides a method of producing a multi-layer coated material. The method comprises coating a first layer of molecules onto a surface of a substrate through covalent bounds, electrostatic interactions, or combinations thereof; and coating a second layer of molecules onto said first layer through covalent bounds, electrostatic interactions, or combinations thereof.

In a specific embodiment, the method further comprises surface activating the substrate, using means such as, but not limited to, chemical treatment, plasma discharge, corona discharge, electron-beam, and combinations thereof.

Specific materials that can be used as the substrate for the method include, but are not limited to, metals, alloys, ceramic materials, glasses, carbon, silicon, and polymers. The substrate may be solid or porous. A specific substrate material is a sintered porous polymer.

Specific polymers that can be used as the substrate for the method include, but are not limited to, polyolefin, polyester, polyurethane, polycarbonate, polyetheretherketone, poly(phenylene oxide), poly(ether sulfone), and nylon. Specific examples of polyolefin include, but are not limited to, ethylene vinyl acetate, ethylene methyl acrylate, polyethylene, polypropylene, ethylene-propylene rubber, ethylene-propylene-diene rubbers, poly(1-butene), polystyrene, poly(2-butene), poly(1-pentene), poly(2-pentene), poly(3-methyl-1-pentene), poly(4-methyl-1-pentene), 1,2-poly-1,3-butadiene, 1,4-poly-1,3-butadiene; polyisoprene, polychloroprene, poly(vinyl acetate), poly(vinylidene chloride), poly(vinylidene fluoride), poly(tetra fluoro ethylene), and mixtures thereof.

In another specific embodiment of the method, the molecules of the first layer and the second layer are independently polyelectrolytes, surfactants, neutral polymers, small molecules, biomolecules, and combinations thereof. In another embodiment, the method further comprising coating one or more additional layers of molecules onto the second or the additional layer through covalent bounds, electrostatic interactions, or combinations thereof.

5. BRIEF DESCRIPTION OF THE DRAWINGS

To better understand specific novel aspects of the invention, reference can be made to the figures described below:

FIG. 1 provides a general schematic of various embodiments of the invention having a two-layer coating, wherein molecules that make up a coating are indicated by circles, circles without a plus or a minus indicate a neutral molecule, circles with a "+" indicate a cationic molecule or a molecule containing a cationic moiety, and circles with a "−" indicate a anionic molecule or a molecule containing an anionic moiety;

6. DETAILED DESCRIPTION

This invention is directed, in part, to materials having multilayer coatings, and in particular to porous materials having multilayer coatings. The invention is further directed to methods of making such materials and to methods of modifying the surface properties of porous and solid materials. Specific materials of the invention are durable, have controlled wicking properties, and unique physical and chemical surface properties.

Materials of this invention can be used as filters, films, lateral flow membranes, conjugate pads, extraction materials, and blood separation materials. Therefore, the applications of the present invention's materials include, but are not limited to, filtration and extraction devices, chromatographic devices such as thin-layer chromatographic devices, lateral flow devices, flow through devices, fast screening devices, combinatory chemistry matrix, microfluidic devices, and cell culture materials.

Specific materials of this invention can be produced economically and/or consistently and can exhibit one or more of the following properties: permanent hydrophilicity or hydrophobicity; high density functional groups; limited leaching; strong and/or specific binding ability to a variety of reagents such as proteins and other biomolecules; controllable and/or narrower distribution of porosities; controllable and wide wicking rates; flexible strength for different applications.

Materials of the invention can be made into sheets or membranes of various thicknesses and shapes. In a specific embodiment, the thickness of the material ranges from about 1 μm to about 10 mm. In another embodiment, the thickness ranges from about 1 μm to about 1 mm. More specifically, the thickness ranges from about 10 μm to about 500 μm. The materials of the invention can also be made into various shapes according to the specific device and assay desired.

In another specific embodiment, the material of this invention has a low surface tension, e.g., below about 50 dynes/cm, more typically below about 40 dynes/cm. In other specific embodiments, the material comprises wetting agents or is surface activated and then coated with one or more layers of a polyelectrolyte, a surfactant, a neutral polymer, a small molecule, a biomolecule, or a combination thereof. Functional groups are attached to a surface of particular materials of the invention that can be used to covalently and/or electrostatically bind other molecules (e.g., target molecules) onto the surface. Examples of target molecules include, but are-not limited to, enzymes, proteins, cells, nucleic acids, peptides, ligands, DNA and RNA.

Figure 1:
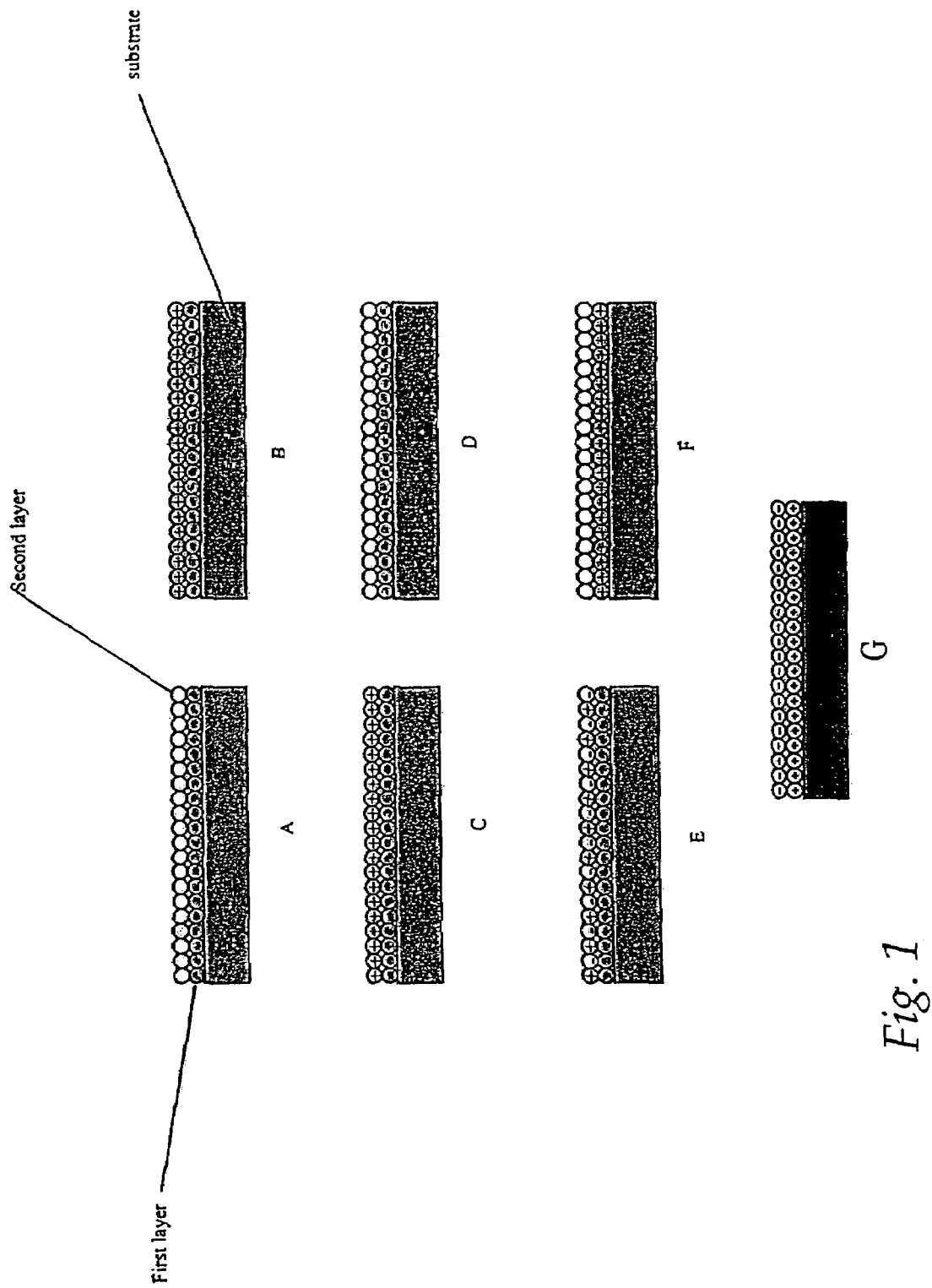

The material encompassed by one embodiment of the invention is illustrated in FIG. 1. This material comprises a porous substrate with at least one surface being coated with a multi-layer coating. Each layer of the multilayer coating can be neutral (e.g., as shown in FIG. 1A) or can contain localized and/or net cationic or anionic charges (e.g., as shown in FIGS. 1B, 1C, 1D, 1E, and 1F). The layers can be adhered to the substrate surface and to each other by covalent and/or electrostatic interactions. For example, molecules forming the layer in direct contact with the substrate (first layer) can be covalently bound to its surface, and molecules forming the second surface (second layer) can be adhered to the first surface by electrostatic interactions (e.g. as shown in FIG. 1B). Other scenarios include first layer electrostatic interactions/second layer covalent bound; first layer covalent bound/second layer covalent bound; first layer electrostatic interactions/second layer electrostatic interactions; and mixed covalent bound and electrostatic interactions for both first and second layers. Because the molecules forming each layer can bond to the material below it by multiple covalent and/or electrostatic interactions, typical materials of the invention have highly stable coatings that are resistant to delamination and/or dissociation.

6.1. Materials

Materials of the invention, which comprise a substrate and a multilayer coating, can be made using methods described herein from materials such as, but not limited to, those discussed below.

6.1.1. Substrates

Substrates that can be used to provide materials of the invention can be solid or porous, and can come in any of a variety of shapes and forms. For example, substrates can be blocks, films, molded parts, tubes, fibers, and sheets. Preferred porous substrates have an average pore size of from about 0.001 μm to about 1000 μm, more preferably from about 0.01 μm to about 500 μm, and most preferably from about 0.1 μm to about 200 μm.

Solid and porous substrates can be made of a variety of materials, such as, but not limited to: metals (e.g., Cu, Ag, Au, Al, Zn, and Fe); alloys; glasses; ceramics; carbon black; silica; silicon; and polymeric materials or plastics. As used herein, "porous materials" or "porous substrate" refers to a material or a substrate that has a surface with one or more pores or a surface that is uneven, undulating, or not smooth or flat, such as a woven, non-woven, compressed, perforated, or etched material or substrate.

A specific substrate of the present invention is a sintered porous polymeric or plastic material. Porous polymeric materials can usually be made from a variety of thermoplastic and thermoset materials using methods known in the art such as, but not limited to, sintering and casting. According to the present invention, the porous polymeric materials are made through a sintering process, as discussed herein. Thus, suitable polymers for the substrate are those that can be sintered to form sheet or membrane-like porous materials. Examples of suitable thermoplastic or thermoset materials include, but are not limited to, polyolefins, nylons, polycarbonates, nitrocellulose, fiberglass, and poly(ether sulfones).

Examples of polyolefins suitable for the present invention include, but are not limited to, ethylene vinyl acetate (EVA); ethylene methyl acrylate (EMA); polyethylenes such as, but not limited to, low density polyethylene (LDPE), linear low density polyethylene (LLDPE), high density polyethylene (HDPE), and ultra-high molecular weight polyethylene (UHMWPE); polypropylenes; ethylene-propylene rubbers; ethyl-ene-propylene-diene rubbers; polystyrene; poly(1-butene); poly(2-butene); poly(1-pentene); poly(2-pentene); poly(3-methyl-1-pentene); poly(4-methyl-1-pentene); 1,2-poly-1,3-butadiene; 1,4-poly-1,3-butadiene; polyisoprene; polychloroprene; poly(vinyl acetate); poly(vinylidene chloride); poly (vinylidene fluoride); poly(tetra fluoro ethylene); and mixtures and derivatives thereof.

Specific EVA materials include, but are not limited to, those in the Microthene MU® and Microthene FE® series manufactured by Equistar, Houston, Tex., such as Microthene MU 763-00 (9% vinyl acetate) and Microthene FE 532-00 (9% vinyl acetate). Specific EMA materials include, but are not limited to, those in the Optema TC® series manufactured by Exxon Chemical Company, Baton Rouge, La., such as Optema TC-110 (21.5% methyl acrylate). Specific polyethylene materials include, but are not limited to, those in the Exact® series manufactured by Exxon Chemical Company, such as Exact SLX-9090, Exact 3024, Exact, 3030, Exact 3033, Exact 4011, Exact 4041, Exact SLP-9053, Exact SLP-9072, and Exact SLP-9095. Specific examples of LDPE include, but are not limited to, those in the 20 series manufactured by DuPont Chemical Company, Wilmington, Del., such as 20 series 20, 20 series 20-6064, 20 series 2005, 20 series 2010, and 20 series 2020T. Specific examples of LLDPE include, but are not limited to, those in the Exact® series manufactured by Exxon Chemical Company, such as Exact 3022 and Exact 4006. Specific examples of HDPE include, but are not limited to, those in the Escorene HX® series manufactured by Exxon Chemical Company, such as Escorene HX-0358.

Ultra-high molecular weight polyethylenes include, but are not limited to, UHMWPE having a molecular weight greater than about 1,000,000. Typically, UHMWPE displays no measurable flow rate under normal test procedures. See, U.S. Pat. No. 3,954,927. Ultra-high molecular weight polyethylene also tends to have enhanced mechanical properties compared to other polyethylenes, including, but not limited to, abrasion resistance, impact resistance and toughness. Polyethylenes having weight average molecular weights of 1,000,000 or higher, which are included within the class designated as UHMWPE, typically an intrinsic viscosity in the range of about 8 or more. Specific examples of UHMWPE include, but are not limited to, Hostalen GUR® sold by Ticona Inc., League City, Tex.

Polypropylenes include, but are not limited to, the Polyfort® series manufactured by A Shulman Co., Akron, Ohio, such as FPP 2320E, 2321E, 2322E, 2345E, PP2130, and PP2258; the Acctuf® series manufactured by BP Amoco Corporation, Atlanta, Ga., such as Acctuf 3045, Amoco 6014, and Amoco 6015; the Aristech® series manufactured by Aristech Chemical Corp., Pittsburgh, Pa., such as D-007-2, LP-230-S, and TI-4007-A; the Borealis® series manufactured by BASF Thermoplastic Materials, Saint Paul, Minn., such as BA101E, BA110E, BA122B, BA204E, BA202E, and BA124B; the Polypro® series manufactured by Chisso America Inc., Schaumburg, Ill., such as F1177 and F3020; the Noblen® series manufactured by Mitsubishi Petrochemical Co. Ltd., Tokyo, Japan, such as MA8; the Astryn® series manufactured by Montell USA Inc., Wilmington, Del., such as 68F4-4 and PD451; the Moplen® series manufactured by Montell USA Inc., such as D 50S, D 60P, and D 78PJ; and the Pro-Fax® series manufactured by Montell USA Inc., such as 6723, 6823, and 6824.

A specific substrate material of this invention is sintered porous polymeric material, which can be surface activated and/or coated with one or more layers of a variety of materials. Depending on its manufacturing process, a porous polymeric material can thus contain regular arrangements of channels and pores of random and/or well-defined diameters and/or varying shapes and sizes.

As a practical matter, the term "pore" is an artificial one that can have various meanings. According to the present invention, the average sizes, shapes, and number of pores in a material can be determined by taking a cross-section of the material. For the purpose of this invention, holes and depressions in the cross-section are considered pores. And, while only two-dimensional sizes and shapes of those pores can be determined from the cross-section, information about their third dimension (e.g. their depth) can be determined from a second cross-section, orthogonal to the first. Also, average pore size, pore volume, and/or surface area can be inferred from measurements obtained using a mercury intrusion porisometer. For the purpose of this invention, pore sizes are typically referred to in terms of their average diameters, even though the pores themselves are not necessarily spherical.

The particular method used to form the pores or channels of a porous polymeric material and the resulting porosity (i.e., average pore size and pore density) of the porous material can vary according to the desired application for which the final membrane be used. The desired porosity of the matrix can also be affected by the polymeric material itself, as porosity can affect in different ways the physical properties (e.g., tensile strength and durability) of different materials.

A specific porous polymeric material of this invention has an average pore size of from about 0.1 µm to about 200 µm, more specifically from about 1 µm to about 50 µm, and from about 1 µm to about 20 µm. For purpose of this invention, pore size and pore density can be determined using, for example, a mercury porisometer, scanning electron microscopy, or atomic force microscopy.

Although the porous polymeric material of the present invention can be made from the materials discussed above, many other materials that are commercially available can also be used for the purposes. Suitable substrates can be purchased from Porex Technologies, Fairburn, Ga.

6.1.2. Coatings

The multilayer coatings of the present invention comprise at least two layers, the first of which is adhered (e.g. covalently and/or electrostatically) to the surface of the substrate, and the second of which is adhered (e.g., covalently and/or electrostatically) to the first layer. Using methods and materials disclosed herein as well as ones known to those of skill in the art, additional layers can be adhered atop the second layer and to one another (e.g., covalently and/or electrostatically).

The substrate of the present invention can be coated with one or more layers of coating to make a material suitable for use in a wide variety of applications, such as analyte detection. In a specific embodiment, a sintered porous plastic substrate is surface activated, as discussed herein, before being coated.

Examples of the materials that can be used as the first layer, second layer, or further additional layers include, but are not limited to, charged polymers or polyelectrolytes, surfactants, neutral polymers, small molecules, biomolecules, and combinations thereof. Some of the charged polymers contain a net cationic or anionic charge, or localized cationic or anionic charges (e.g., zwitterions), or can provide net or localized charges when adhered or deposited onto the substrate and/or layer(s) coating the substrate. For example, layers can be formed from organic or inorganic salts.

Organic materials that can be used to form coatings of the invention include, but are not limited to, organic polymers, monomers, and biomolecules. Preferred organic materials contain net and/or localized cationic or anionic charges. Organic materials that are-preferred for direct adhesion to the surface of a substrate are polymers, such as, but not limited to, single and copolymers (e.g., random, graft, and block copolymers). Polymers used in coating in the present invention have a molecular weight of from about 1,00 to about 5 million, preferably, from about 10,000 to about 2 million.

Specific examples materials from which first, second, and additional layers can be formed are materials that contain a net cationic or anionic charge, or localized cationic or anionic charges (e.g., zwitterions), or can provide net or localized charges when adhered or deposited onto the substrate and/or layer(s) coating the substrate. For example, layers can be formed from organic or inorganic salts.

Materials that can be used for direct adhesion to the surface of a substrate include polymers, such as, but not limited to, single and copolymers (e.g., random, graft, and block copolymers). Polymers used in coating in the present invention have a molecular weight of from about 1,00 to about 5 million, preferably, from about 10,000 to about 2 million.

In a specific embodiment of the present invention, materials for the first layer and second layer include, independently, one or more of a surfactant, phosphate, polyethyleneimide (PEI), poly(vinylimidazoline), quaterized polyacrylamide, polyvinylpyridine, poly(vinylpyrrolidone), polyvinylamines, polyallylamines, chitosan, polylysine, poly(acrylate trialkyl ammonia salt ester), cellulose, poly(acrylic acid) (PAA), polymethylacrylic acid, poly(styrenesulfuric acid), poly(vinylsulfonic acid), poly(toluene sulfuric acid), poly(methyl vinyl ether-alt-maleic acid), poly(glutamic acid), dextran sulfate, hyaluric acid, heparin, alginic acid, adipic acid, chemical dye, protein, enzyme, nucleic acid, peptide, or a salt or ester thereof. More specifically, materials for the first layer include a polyethyleneimide, poly(vinylpyrrolidone), or combinations thereof.

Examples of polymers or copolymers that contain cationic charges include those that contain quaternary groups of nitrogen and phosphor, polymers that contain primary and secondary amine groups. These polymers can be charged in certain range of pH in solutions. Particular examples include, but are not limited to, surfactants, polyethyleneimide (PEI), poly (vinylimidazoline), quaterized polyacrylamide, polyvinylpyridine, poly(vinylpyrrolidone), polyvinylamines, polyallylamines, chitosan, polylysine, poly(acrylate trialkyl ammonia salt ester), cellulose, and salts thereof.

Examples of polymers or copolymers that contain anionic charges include, but are not limited to, poly(acrylic acid) (PAA) and its sodium salt, polymethylacrylic acid and its sodium salt, poly(styrenesulfuric acid) (PSSA) and its sodium salt, celluloses that contain sulfonated or carboxylic acid groups, poly(vinylsulfonic acid), poly(toluene sulfuric acid), poly(methyl vinyl ether-alt-maleic acid) and ester, poly (glutamic acid), dextran sulfate, hyaluric acid, heparin, alginic acid, adipic acid, sodium carboxymethyl cellulose (CMC), anionic charged polymer surfactants, and molecules containing a phosphate group.

Polymers and copolymers that contain both cationic and anionic moieties can also be used to provide materials of this invention. For example, about one to about 99 percent of the repeat units of a polymer can contain cationic moieties, preferably from about 20 to 80 percent. Amphoteric polymers (i.e., polymers wherein about 50 percent of the repeat units contain cationic groups and about 50 percent contain anionic groups) can also be used. Polymers and copolymers may have varying charge densities (i.e., the ratio of charge to the number of repeat units). For example, polymers with charge densities of from about one to 100 percent, preferably from about 20 to about 100 percent, can be used.

Neutral polymers can also be used to form the multilayer coatings of the invention, particularly polymers capable of forming covalent bonds with the components of other layers or with the substrate surface under conditions such as those discussed herein. Examples of such neutral polymers include, but are not limited to: isocyannated terminated polymers, including polyurethane, and poly(ethylene glycol) (PEG); epoxy-terminated polymers, including PEG and polysiloxanes; and hydroxylsuccimide terminated polymers.

Small molecules can also be used to provide layers and coatings of the invention. Specific small molecules encompassed by the present invention have a molecular weight of from about 10 to about 10,000. More specifically, the molecular weight of the small molecules ranges from about 50 to about 2,000 and from about 50 to about 1,000. Preferred small molecules are charged. Examples of small molecules include, but are not limited to, s surfactant, such as zonyl surfactant (DuPont), SURFYNOL(Air product), FLUORAD (3M), sodium dodecylsulfonate (SDS), dodecyltrimethylamonium bromide (DTAB), phosphates, sulfonates, bronates, sulfonates, dyes, lipids, and metal ions. Small molecules also include other specific surfactants such as cationic surfactants, anionic surfactants, amphoteric surfactants, and fluorine containing surfactants.

Coatings of the invention can also be made from biomolecules. Preferred biomolecules contain net or localized charges. Examples of biomolecules include, but are not limited to, proteins, enzymes, lipids, hormones, peptides, nucleic acids, oligonucleic acids, DNA, RNA, sugars, and polysaccharides. Examples of proteins include, but are not limited to, immunoglobulins G (IgGs) and albumins, such as bovine serum albumin (BSA) and human serum albumin.

6.2. Process of Making the Materials

Materials of the invention can be readily prepared using methods described herein. In a specific method, the surface of a substrate is activated using chemical treatment, plasma, electron-beam (e-beam), and/or corona discharge methods known in the art. This activation alters the surface by cleaving chemical bonds to allow the formation of hydrophilic and/or chemically active moieties such as, but not limited to, hydroxy, amine, and carboxylic groups. Of course, the particular groups formed will depend on the chemical composition of the substrate surface and the methods and conditions used to activate it. Often, the activation of a hydrophobic plastic surface will provide a hydrophilic, electrically charged surface.

Of the various methods that can be used to activate a substrate surface, plasma treatment and corona discharge are preferred for the activation of plastics, and porous plastics in particular. Plasmas that can be used to provide negatively charged porous plastic surfaces include, but are not limited to, plasmas of argon, oxygen, nitrogen, methanol, ethylene oxide, and acetone. Plasmas that can be used to provide positively charged surfaces include, but are not limited to, ammonia and ethylenediamine. Depending on the composition of the substrate, it size, and the particular plasma used, the time necessary to achieve a desired surface will vary. Typical times can vary from about 1 minute to about an hour. Similarly, the power necessary to achieve the desired plasma will typically vary from about 50 W to about 1000 W.

6.2.1. Sintering

A specific embodiment of this invention uses porous plastic substrates made through sintering. Many suitable sintering process of making a porous polymer can be used to form the sintered porous polymeric material of the present invention. Sintering is a process that fuses discrete particles, such as polymer particles, together by heat. For example, polymer particles can be first packed in a mold or other containers or substrates. The particles are then heated to a temperature that usually melts only the outer surface or shell of the particles. The particles are then fused together at this temperature and cooled down to a lower temperature, such as room temperature, to form the sintered product.

In a specific embodiment, the polymeric particles are made using underwater pelleting, e.g., as disclosed in U.S. patent application Ser. No. 09/447,654 of Yao et al., filed Nov. 23, 1999, the content of which is incorporated herein by reference.

According to one embodiment the present invention, a mixture is first formed that comprises the polymeric material (e.g., particles of polymers as discussed in Section 6.1) and other optional materials (e.g., wetting agents and surfactants). The materials are preferably in powder form, and are mixed to ensure an even distribution of each throughout the mixture.

The mixture is then heated to the sintering temperature of the material, optionally under pressure, to provide a sintered porous polymeric material.

Those skilled in the art will recognize that the average pore size of the porous polymeric material will depend, at least in part, on the average particle size of the polymeric material, the sintering temperature, and the pressure—if any—applied to the mixture during sintering. If the particles of the other optional materials, if any, are smaller than the average pore size of the porous material they will be trapped within pores of the material during the sintering process, and may be adhered to the walls of those pores. If particles of the other optional materials, if any, are larger than the average pore size of the porous material, they will be incorporated within the porous material as inclusions.

Sintering can occur on a solid support or within a mold to yield a final product that can be cut into pieces of desired shape. The use of molds is preferred where the desired shape of the self-sealing medium is complex.

6.2.2. Surface Activation

In order to coat a surface of some substrates, it is preferred that the surface be activated before the coating is applied.

The surface of a substrate can be activated using one or more methods known in the art such as, but not limited to, chemical treatment, plasma discharge, electron-beam (e-beam) discharge, and corona discharge. This activation alters the surface of the substrate, by means such as cleaving chemical bonds, to allow the formation of hydrophilic and/or chemically active moieties such as, but not limited to, hydroxy, amine, and carboxylic groups. As one of ordinary skill in the art understands, the particular functional groups formed will depend on the chemical composition of the substrate surface and the methods and conditions used to activate it. Often, the activation of a hydrophobic plastic surface usually provides a hydrophilic, electrically charged surface.

Of the various methods that can be used to activate the surface of a polymeric material, plasma treatment and corona discharge are particularly suited for the activation of the substrate of the present invention. Plasmas that can be used to provide negatively charged porous plastic surfaces include, but are not limited to, plasmas of argon, oxygen, nitrogen, methanol, ethylene oxide, and acetone. Plasmas that can be used to provide positively charged surfaces include, but are not limited to, ammonia and ethylenediamine. Depending on the composition of the substrate, its size, and the particular plasma used, the time necessary to achieve a desired surface will vary. Typical times can vary from about 1 minute to about an hour. Similarly, the power necessary to achieve the desired plasma may vary from about 50 W to about 1000 W.

6.2.3. Coating

The substrate of the present invention, whether or not surface activated, may be coated with various materials. When the substrate is a sintered porous polymeric material the substrate may already contain solid wetting agents, which are added during the manufacturing/sintering process. Wetting agents suitable for use in the present invention include, but are not limited to, surfactants and hydrophilic polymers.

Wetting agents may also be coated onto the surface of the substrate through solution coating methods such as, but not limited to, dipping, spraying, and/or rinsing.

Specifically, the method of coating includes dipping/immersing the substrate into the solution. As understood by one of ordinary skill in the art, means and durations used for the coating process depend on the specific material and the wetting agent involved. Typically, a coating, e.g. immersing, for a duration of from about 0.5 to about 50 minutes is sufficient to provide a coating. In certain cases, a coating duration from about 2 to about 20 or about 2 to about 10 minutes is sufficient. After the coating, the material may then be dried and/or rinsed, after which it mat be coated again, if desired.

In a specific embodiment of the present invention, a sintered porous polymeric material being used as substrate is coated with a polyelectrolyte, a surfactant, a neutral polymer, a small molecule, a biomolecule, or combinations thereof. More specially, the polymeric material is surface activated before being coated.

The surface activated substrate is contacted with a solution of the material(s) from which the first layer will be formed on the surface of the substrate. Specific suitable solutions are solutions of cationic or anionic polymers. The solutions can be aqueous, but organic solvents can also be used. Specific examples are solutions of water, ethanol, isopropanol, and mixtures thereof The contact between the activated substrate and the solution is maintained for a sufficient time and at a sufficient temperature for a first layer to form on the substrate surface. Specifically, layers are formed by the formation of covalent bonds and/or electrostatic interactions between functional groups on the substrate surface and molecules in the solution.

The interactions between functional groups on the substrate surface and molecules in the solution can be adjusted by the type of solvent used, temperature, pH and the addition of coupling agents (e.g., DCC and EDC). For example, high pH and coupling agent concentration can promote covalent bond formation between the substrate and the first layer of coating.

After the resulting coated substrate is removed from the solution, it is washed with, for example, deionized water in an ultrasonic bath. Typical wash times will vary depending on the solvent and the material(s) used to form the first layer, but are often about 10 minutes or less. The washed, single-layer coated substrate can be optionally dried (e.g., at an elevated temperature). Elevated temperature promotes formation of covalent bonds.

The single-coated substrate is next contacted with a second solution. Preferably, this second solution is of molecules that are of an opposite charge to those that form the first layer so that the second layer adheres to the first via electrostatic interactions. However, the first layer can also be formed from molecules that have functional groups that, with or without activation, can react with functional groups on the molecules used to form the -second layer. After the resulting dual-coated substrate is removed from the second solution, it is preferably washed and dried (e.g. at an elevated temperature).

Specific examples of solutions from which the first and second layers can be formed include, but are not limited to, polyelectrolyte solutions of a concentration of about 10 ppm to-about 100,000 ppm. As those of ordinary skill in the art will appreciate, the concentration of any particular solution depends on the polymer molecular weight, charge density and type of molecules from which a given layer is to be made. Solutions of higher molecular weight molecules generally require lower concentrations than those of lower molecular weight molecules. Similarly, high ionic density polymers typically require lower solution concentrations. Generally, biomolecules show high immobilization on a surface with opposite electric charges, particularly when the media is of low ionic strength.

Electrostatic interaction is one of the most important interactions between differently charged polyelectrolytes, especially during complex formation. Different polyelectrolytes can also form covalent bonds between their functional groups. For example, the amino group in PEI can form amide bond with the carboxylic acid group in PAA. The formation, strength, and durability of the covalent bonds also depends on type of solvent, temperature, pH and coupling agents. The ratio of PEI and PAA and the coupling agent will also have an effect on the percentage of covalent bond formed. Coupling reagents, such as dicyclohexylcarbodiimide (DCC) and 1-ethyl-3-(3-dimethylaminopropyl)carbodiimide (EDC), can be used to promote such reactions.

Examples of different coating scenarios include electrostatic interactions between substrate and first layer and covalent bond between first layer and second layer; covalent bond between substrate and first layer and covalent bond between first layer and second layer, electrostatic interactions between substrate and first layer and electrostatic interactions between first layer and second layer; and mixed covalent bond and electrostatic interactions for both coatings. Because the molecules forming each layer can bond to the material below it by multiple covalent and/or electrostatic interactions, typical materials of the invention have highly stable coatings that are resistant to delamination and/or dissociation. Furthermore, the high stability of the present invention's multilayer coating results in lower solubility of the coatings and, thus, provides coatings with low leaching.

In one specific embodiment of the present invention wherein the substrate has been surface activated and further contains two sequentially coated layers, the first layer comprises molecules of polyethyleneimide (PEI) and the second layer comprises molecules of a poly(acrylic acid), a copolymer containing poly(acrylic acid), or a surfactant, such as a surfactant containing fluorine. Alternatively, the first layer comprises molecules of polyallylammoniumchloride and the second layer comprises molecules of polyvinylsulfate. Specific surfactants include, but are not limited to, cationic surfactants, anionic surfactants, amphoteric surfactants, and fluorine containing surfactants.

The process of optionally activating a surface and contacting it with a solution of one or more compounds under conditions sufficient to form a layer on the surface can be repeated to achieve coatings of more than two layers. Thus, multilayer coatings of varying thicknesses, density, and uniformity can be adhered to the surfaces of a variety of substrates.

For example, in one embodiment of the present invention, the substrate, such as a sintered porous polymeric material, is surface activated and further contains two sequentially coated layers. The material is further coated with one or more additional layers bound to the second or the additional layer through covalent bounds, electrostatic interactions, or combinations thereof. In a specific embodiment wherein a polymeric material having been coated with three layers, the first layer comprises molecules of polyethyleneimide, the second layer comprises molecules of a poly(acrylic acid), and the third layer comprises of molecules of polyethyleneimide, polyvinylamine, or a surfactant.

The manufacture of the materials of the invention often requires the formation of functional groups on the surface of a substrate. However, the utility of many materials of the invention may also depend on the number and types of chemical moieties on the surfaces of the final products. Methods of this invention can provide substrates with a variety of chemically reactive functional groups. By way of example, functional groups that can be introduced onto the surfaces of plastic (e.g., porous plastic) substrates include amino groups (including primary, secondary and tertiary amines), which can be positively charged at neutral pH. Amino-functional porous materials can be manufactured by: coating PEI or other amino group containing polyelectrolytes on porous materials; pre-activating materials with plasma, e-bean, or corona glow, and then solution treat porous material with amino containing polyelectrolytes, such as PEI and other amino containing positive charges polyelectrolytes; or solution treat porous materials that already be coated with negative charged polyelectrolytes, such as PAA with amino-containing positive charge electrolytes.

Carboxylic acid groups can be introduced onto porous materials by treating positive charged porous materials with PAA or other carboxylic acid containing polyelectrolytes solutions. Typically, positively charged materials have either been treated with a positively charged polyelectrolyte or have been activated in ammonia solution or ammonia plasma.

Sulfuric acid functional groups can be introduced onto porous materials by treating positive charged porous materials with PSSA or other sulfuric acid containing polyelectrolytes solutions. Typically, positively charged materials have either been treated with a positively charged polyelectrolyte or have been activated in ammonia solution or ammonia plasma.

Poly(ethylene glycol) (PEG) molecules can be coated onto charged porous materials by treating charged porous materials with PEG molecules that contains functional groups with opposite charges. For example, a PEG molecule having a carboxylic acid functional group can be coated onto a porous material coated with PEI.

Biomolecules can also be coated onto the substrates of this invention. For example, biotin, which is a small biomolecule that can specifically binds to avidin and streptavidin, can be introduced onto porous materials by treating charged porous materials with the biotin derivatives that contain opposite charges as compared to the porous materials.

Many polysaecharides contain electric charges and can provide good matrices for cell growth and harvesting. These charged polysaccharides, such as heparin, chitosan, and CMC, can be introduced onto porous materials by treating oppositely charged porous materials with the polysaccharides.

Fluoroalkyl groups, such as perfluoroalkyl groups, can be attached to porous materials by treating charged porous materials with fluoroalkyl molecules that contain opposite charges.

6.3. Characteristics and Testing of Materials

A preferred embodiment of the invention comprises a substrate and at least two coating layers of polymers, wherein one of the polymers contains cationic charge and another of the polymers contains anionic charge. Such as, PEI and PAA, PEI and PSSA Without being limited by theory, it is believed that the adhesion of a second, oppositely charged layer to the first can provide a coating that is substantially more stable than the first layer alone due to the large number of electrostatic interactions between the two layers and the low solubility of the material.

The present invention also encompasses materials having multilayer coatings of three or more layers adhered to the surface of a substrate (preferably a porous plastic substrate). Such multilayer complexes can be constructed, for example, by the repeated application of compounds of opposite electric charges. Examples of such complexes include, but are not limited to: PEI/PAA/PEI/PAA/ . . . , PEI/PAA/polyallylamide/polystyrenesulfonate/ . . . , PEI/protein/PAA/protein/ . . . , and PEI/biomolecule/PAA/biomolecule/ . . . (wherein ". . . " indicates the possible existence of additional layers).

Depending on the use to which a particular material is put, a wide variety of small and large molecules can be used to provide coating layers of the invention. Various effects several classes of such molecules are discussed below.

6.3.1. Metal Ions

Small metallic and organic ions can be immobilized within the matrix provided by a charged polymer-based first layer. Many metal ions can complex with PEI or PAA, and some ions (especially high charged ones) can be immobilized within layers of the materials of the invention: Examples of such complexes include, but are not limited to: PEI/PAA/metal ion/PEI/ . . . and PEI/anionic ions/PEI/ . . . .

Because most polyelectrolytes are excellent coordinators for heavy metal ions, materials of this invention can include layers of cationic or anionic polymers in which heavy metal ions are trapped. Inorganic ions can also be used to bridge different polyelectrolyte layers onto porous materials. Examples include, but are not limited to: PEI/native charge ions/PEI/Negative charge ion/PEI and PEI/PAA/Positive charge ions/PAA/positive charge ions. Table 1 shows the effect copper ions can have on the color of porous plastic-based materials of the invention:

TABLE 1

Copper ions immobilization on porous plastics

| | Surface | | | | |
|---|---|---|---|---|---|
| | Oxygen plasma | PEI | PEI/PAA | PAA | PAA/PEI |
| Color | white | blue | dark blue | light blue | dark blue |

6.3.2. Dye Molecules

Small molecules that be incorporated within, or used to form one or more coating layers include organic and inorganic dyes, particularly dyes with electric charges. Such dyes can be used to provide materials useful as indicators of chemical reactions, pH, and other environmental conditions.

Most dye molecules are charged molecules and have strong interactions with polyelectrolytes. Dye molecules can be immobilized onto porous materials through polyelectrolyte coating. The immobilized dye can provide porous material with desired color and optical property. The color change of immobilized dye on porous material provides application possibility of using porous material as sensors.

TABLE 2

Rf values for dyes on differently treated porous plastics.

| Surface | Rf Nile blue (cationic) | Rf Poncreas (anionic) | Rf Acridin orange (cationic) |
|---|---|---|---|
| Oxygen plasma | 0 | 0.8 | 0 |
| PEI | 0.65 | 0.1 | 0.5 |
| PEI/PAA | 0 | 0.2 | 0.2 |

6.3.3. Surfactants

Small charged organic surfactants can also be incorporated into materials of the invention, and can be used to provide oleophobic porous materials and control the wicking rates of porous materials in different solvents. The combination of surfactants and charged polymers can result in stable, oleophobic surfaces that exhibit little leaching.

Small molecular surfactant with negative charges can be immobilized onto positive polyelectrolytes coated porous plastic, such as, PEI coated porous materials. Small molecular surfactant with positive charges can be immobilized onto negative polyelectrolytes coated porous plastic, such as, PAA coated porous materials.

Amphoteric small molecular surfactant can be immobilized onto all kind polyelectrolyte coated porous materials, including, negative, positive and the complex.

TABLE 3

Wicking rates for Zonyl surfactant treated porous plastics.*

| | PSN | | FS62 | | PSA | | PSK | | FSP | |
|---|---|---|---|---|---|---|---|---|---|---|
| Surface | water | ethanol | water | ethanol | water | ethanol | water | ethanol | water | ethanol |
| Oxygenplasma | 140 | 120 | 120 | 160 | 360 | 140 | No | 220 | No | 260 |
| PEI | 120 | 110 | 270 | 270 | No | 140 | 80 | 140 | No | 1020 |
| PEI/PAA | 100 | 110 | 360 | 320 | No | 245 | 150 | 90 | No | No |

*Numbers are seconds/4 cm.
"No" indicates no wicking occurred.

6.3.4. Biological Molecules

Biological molecules ("biomolecules") can also be used to form one or more coating layers on solid and porous substrates, thereby providing materials useful in applications such as, but not limited to, affinity binding assays, PCR substrates, and drug delivery devices. Within the meaning of the present invention, biomolecules include, but are not limited to, proteins, enzymes, peptides, DNA, and RNA. Preferred biomolecules are locally charged biomolecules, which can be electrostatically adhered to a first or subsequent layer bound to a substrate invention. Biomolecules can be adsorbed onto the surface of a charged first or subsequent layer (i.e., to form the outermost layer of a material of the invention), directly adhered to the substrate to form a first layer of a material, or trapped between two or more layers. Of course, as with any of the other molecules that can be used to provide materials of the invention, how and where a particular biomolecule is incorporated into a material depends on the intended us of the material and the biomolecule itself (e.g., its size, structure, and charge).

For example, biomolecules with negative charges can be directly adsorbed onto layers of positively charged surfaces, such as PEI, and can be further stabilized with another layer of polyelectrolytes, such as PAA or PEI. Negative charged biomolecules can also be mixed with PAA in a solution used to form a first or subsequent coating layer atop a substrate of the invention. Such mixtures can add to the chemical and physical (e.g., susceptibility to leaching) stability of biomolecules that form materials of the invention. Similarly, biomolecules that have distinct cationic and anionic ends can be incorporated into complexes such as, but not limited to, PEI/Biomolecule/PAA.

Multiple biomolecule-based layers can also be prepared using methods of the invention. Examples include, but are not limited to: PEI/negative charged biomolecule/PEI/negative charged biomolecule/ . . . and PEI/PAA/positive charged biomolecules/PAA/positive charged biomolecules.

6.4. Applications

Materials of this invention have a wide variety of applications. For example, specific materials of the invention exhibit stable and uniform wicking rates, and show limited leaching in pure water. Such materials can be used in filtration and other liquid delivery devices.

The invention further encompasses oleophobic-coated materials. For example, porous plastics can be prepared using methods of the invention that have a first coating of a polyelectrolyte (e.g., PEI) and an oppositely-charged second coating made from a charge-containing fluorinated surfactant. Such materials may be used in aeration devices and other devices that allow air, but not liquid, permeation.

The materials of the present invention can also be used to aid in the delivery, screening, extraction, separation, or purification of various molecules, including biomolecules. For example, the biomolecule binding ability of porous plastic-based PEI/PAA materials are highly dependent on solution media, and can therefore be used to extract particular biomolecules from solution. The release of biomolecules from materials of this invention can also be controlled as to depend on surrounding solvent conditions such as, but not limited to, pH and ionic strength. Therefore, the materials of the present invention can be used in biomolecule purification, DNA/RNA extraction, biofluid-purification, lateral flow devices, microfluidic devices, and fast screening devices.

Materials of the invention can also be used as filters in a variety of applications, including medical applications, where chemical leaching and contamination are unacceptable. The porous plastic-based PEI/PAA materials of the invention show limited leaching in aqueous solution. Chromatography is another application to which materials of the invention can be put. For example, materials can be used to make pre-columns useful to remove impurities and contaminants in HPLC apparatuses and TLC plates. The materials can also be used as ion-exchange columns. A final, non-limiting example of an application to which materials of the invention can be put is any application that requires conductive porous plastics. Such plastics may be of particular use in chemical and bio-assay technology.

7. EXAMPLES

7.1. Example 1

Hydrophilic Surface

A porous plastic sheet made by Porex Corporation (pore size 7 micron, 35% pore volume) was preactivated with oxygen plasma (EURO PLASMA CD600PC) at 100 watt, 120 mm Hg for 5 minutes. The sheet become hydrophilic and has a wicking rate of 60 seconds/4 cm. The pre-activated porous plastic sheet was immersed into 0.1% or 1% of PEI (BASF, MW 750,000) ethanol-water solution for 10 minutes. Then the coated sheet was rinsed with 100 times water in-an ultrasonic bath (VWR) at room temperature for 5 minutes. This washing was repeated three times. The rinsed porous plastic sheet then was immersed into certain concentration of 0.1% or 1% PAA (Aldrich, 523925, MW 250,000) ethanol-water solution for 10 minutes. The coated sheet was washed with 100 times water in an ultrasonic bath (VWR) at room temperature for 5 minutes. This washing was repeated three times. The treated sheet was dried at room temperature.

7.2. Example 2

Hydrophilic Surface

A porous plastic sheet made by Porex Corporation (pore size 7 micron, 35% pore volume) was preactivated with corona discharge (Corotech, Corotreator) at 200 watt for 2 minutes. The sheet become hydrophilic and has a wicking rate of 60 seconds/4 cm. The pre-activated porous plastic sheet was immersed into 0.1% or 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into certain concentration of 0.1% or 1% PAA (Aldrich, 523925, MW 250,000) ethanol-water solution for 10 minutes. The coated sheet was washed with 100 times water in an ultrasonic bath (VWR) at room temperature for 5 minutes. This washing was repeated three times. The treated sheet was dried at room temperature.

7.3. Example 3

Hydrophilic Surface

A porous plastic sheet made by Porex Corporation (pore size 7 micron, 35% pore volume) was preactivated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (B3ASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of poly-DL-aspartic acid, sodium salt (Sigma, 47789-3, MW 3000) ethanol-water solution for 10 minutes. The coated sheet was washed with 100 times water in an ultrasonic bath (VWR) at room temperature for 5 minutes. This washing was repeated three times. The treated sheet was dried at room temperature.

7.4. Example 4

Hydrophilic Surface

A porous plastic sheet made by Porex Corporation (pore size 7 micron, 35% pore volume) was preactivated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of poly(styrenesulfonic acid-co maleic acid), sodium salt (Sigma, 43455-8, MW 20,000) ethanol-water solution for 10 minutes. The coated sheet was washed with 100 times water in an ultrasonic bath (VWR) at room temperature for 5 minutes. This washing was repeated three times. The treated sheet was dried at room temperature.

7.5. Example 5

Hydrophilic Surface

A porous plastic sheet made by Porex Corporation (pore size 7 micron, 35% pore-volume) was preactivated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of poly(vinylsulfate, sodium salt) (Sigma, 27842-4) ethanol-water solution for 10 minutes. The coated sheet was washed with 100 times water in an ultrasonic bath (VWR) at room temperature for 5 minutes. This washing was repeated three times. The treated sheet was dried at room temperature.

7.6. Example 6

Hydrophilic Surface

A porous plastic sheet made by Porex Corporation (pore size 7 micron, 35% pore volume) was preactivated with oxygen plasma (EUROPLASMA, CD 600PC) at 100 watt, 120 nm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 0.01% of carboxymethyl cellulose, sodium salt (Sigma, 41913-1, MW 250,000) 0.01M PBS solution for 10 minutes. The coated sheet was washed with 100 times water in an ultrasonic bath (VWR) at room temperature for 5 minutes. This washing was repeated three times. The treated sheet was dried at room temperature.

7.7. Example 7

Hydrophilic Surface

A porous plastic sheet made by Porex Corporation (pore size 7 micron, 35% pore volume) was preactivated with oxygen plasma (ELROPLASMA, CD 600PC) at 100 watt, 120 mm Hg for 5 minutes. The sheet become hydrophilic and has a wicking rate of 60 seconds/4 cm. The pre-activated porous plastic sheet was immersed into 0.01% of chitosan (Sigma, 448 87-7) 10% acetic acid aqueous solution for 10 minutes. Then the coated sheet was rinsed with 100 times water in an ultrasonic bath (VWR) at room temperature for 5 minutes. This washing was repeated three times. The rinsed porous plastic sheet then was immersed into 0.01% of carboxymethyl cellulose, sodium salt (Sigma, 41913-1, MW 250,000) 0.01M PBS solution for 10 minutes. The coated sheet was washed with 100 times water in an ultrasonic bath (VWR) at room temperature for 5 minutes. This washing was repeated three times. The treated sheet was dried at room temperature.

7.8. Example 8

Hydrophilic Surface

A porous plastic sheet made by Porex Corporation (pore size 7 micron, 35% pore volume) was preactivated with ammonia plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PAA (Sigma, MW 250,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of PEI (BASF, MW 750, 000) ethanol-water solution for 10 minutes. The coated sheet was washed with 100 times water in an ultrasonic bath (VWR) at room temperature for 5 minutes. This washing was repeated three times. The treated sheet was dried at room temperature.

7.9. Example 9

Hydrophilic Surface

A porous plastic sheet made by Porex Corporation (pore size 7 micron, 35% pore volume) was preactivated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of poly (diallyldimethylammonia chloride) (Sigma, 40903-0, MW 500,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of poly(vinylsulfate, sodium salt) (Sigma, 27842-4) ethanol-water solution for 10 minutes. The coated sheet was washed with 100 times water in an ultrasonic bath (VWR) at room temperature for 5 minutes. This washing was repeated three times. The treated sheet was dried at room temperature.

7.10. Example 10

Hydrophilic Surface

A porous plastic sheet made by Porex Corporation (pore size 7 micron, 35% pore volume) was preactivated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of poly(allylamine hydrochloride) (Sigma, 28322-3, MW 15,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of poly(vinylsulfate, sodium salt) (Sigma, 27842-4) ethanol-water solution for 10 minutes. The coated sheet was washed with 100 times water in an ultrasonic bath (VWR) at room temperature for 5 minutes. This washing was repeated three times. The treated sheet was dried at room temperature.

7.11. Example 11

Multi-Layer Positively Charged Hydrophilic Surface

A porous plastic sheet made by Porex Corporation (pore size 7 micron, 35% pore volume) was preactivated with oxygen plasma (EURO PLASMA CD600PC),) at 100 watt, 120 mm Hg for 5 minutes. The sheet become hydrophilic and has a wicking rate of 60 seconds/4 cm. The pre-activated porous plastic sheet was immersed into 0.1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed 0.1% PAA (Sigma, MW 250,000) ethanol-water solution for 10 minutes. The coated sheet was washed with 100 times water in an ultrasonic bath (VWR) at room temperature for 5 minutes. This washing was repeated three times. This PAA coated porous material was immersed into 0.1% of PEI (13ASF, MW 750,000) ethanol-water solution for 10 minutes. Then the coated sheet was rinsed with 100 times water in an ultrasonic bath (VWR) at room temperature for 5 minutes. This washing was repeated three times. The treated sheet was dried at room temperature.

7.12. Example 12

Multi-Layer Negatively Charged Hydrophilic Surfaces

A porous plastic sheet made by Porex Corporation (pore size 7 micron, 35% pore volume) was preactivated with oxygen plasma (EUROplasma CD600PC),) at 100 watt, 120 mm Hg for 5 minutes. The sheet become hydrophilic and has a wicking rate of 60 seconds/4 cm. The pre-activated porous plastic sheet was immersed into 0.1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 0.1% PAA (Sigma, MW 250,000) ethanol-water solution for 10 minutes. The coated sheet was washed with 100 times water in an ultrasonic bath (VWR) at room temperature for 5 minutes. This washing was repeated three times. This PAA coated porous material was immersed into 0.1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. This PEI coated porous plastic sheet then was immersed 0.1% PAA (Sigma, MW 250,000) ethanol-water solution for 10 minutes. The coated sheet was washed with 100 times water in an ultrasonic bath (VWR) at room temperature for 5 minutes. This washing was repeated three times. The treated sheet was dried at room temperature.

7.13. Example 13

Oleophobic Surface

A porous plastic sheet made by Porex Corporation (pore size 7 micron, 35% pore volume) was preactivated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of FSP (DuPont) ethanol-water solution for 10 minutes. The coated sheet was washed with 100 times water in an ultrasonic bath (VWR) at room temperature for 5 minutes. This washing was repeated three times. The treated sheet was dried at room temperature.

7.14. Example 14

Oleophobic Surface

A porous plastic sheet made by Porex Corporation (pore size 7 micron, 35% pore volume) was preactivated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of perfluoro-1-octanosulfonic acid, tetraethylammonium salt (Sigma, 36528-9) ethanol-water solution for 10 minutes. The coated sheet was washed with 100 times water in an ultrasonic bath (VWR) at room temperature for 5 minutes. This washing was repeated three times. The treated sheet was dried at room temperature.

7.15. Example 15

Semi-Conductive Porous Plastic

A porous plastic sheet made by Porex Corporation (pore size 7 micron, 35% pore volume) was preactivated with oxygen plasma (EUROPLASMA, CD 600PC) at 100, watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of poly(anilinesulfonic acid) (Sigma, 52328-3, MW 10,000) ethanol-water solution for 10 minutes. The coated sheet was washed with 100 times water in an ultrasonic bath (VWR) at room temperature for 5 minutes. This washing was repeated three times. The treated sheet was dried at room temperature.

7.16. Example 16

Covalently Bound Polyelectrolyte Complex

A porous plastic sheet made by Porex Corporation (pore size 7 micron, 35% pore volume) was preactivated with oxygen plasma (EUROplasma CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into certain concentration of 0.1% PAA (Sigma, MW 250,000), 0.2 % Dicylohexylcarbodiimide (DCC) (Sigma, D8000-2) DMF solution for 10 minutes. The coated sheet was washed with 100 times water in an ultrasonic bath (VWR) at room temperature for 5 minutes. This washing was repeated three times. The treated sheet was dried at room temperature.

7.17. Example 17

Material Coated with Anionic Dye Molecules

A porous plastic sheet made by Porex Corporation (pore size 7 micron, 35% pore volume) was preactivated with oxygen plasma (EUROPLASMA CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 0.1% anionic dyes, such as Ponceau S, sodium salt (Sigma, P3504) ethanol-water solution for 10 minutes. The coated sheet was washed with 100 times water in an ultrasonic bath (VWR) at room temperature for 5 minutes. This washing was repeated three times. The treated sheet was dried at room temperature.

7.18. Example 18

Materials Coated with Cationic Dye Molecules

A porous plastic sheet made by Porex Corporation (pore size 7 micron, 35% pore volume) was preactivated with oxygen plasma (EUROPLASMA CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% PAA (Sigma, MW 250,000) ethanol-water solution for 10 minutes. The coated sheet was washed with 100 times water in an ultrasonic bath (VWR) at room temperature for 5 minutes. This washing was repeated three times. The treated sheet was dry at room temperature. Coated porous materials then was immersed into 0.1% cationic dyes, such as Acridin Orange (Sigma, A 6014), ethanol-water solution. The coated sheet was washed with 100 times water in an ultrasonic bath (VWR) at room temperature for 5 minutes. This washing was repeated three times. The treated sheet was dried at room temperature.

7.19. Example 19

Material Coated with Poly(ethylene Glycol) (Ionic Interaction)

A porous plastic sheet made by Porex Corporation (pore size 7 micron, 35% pore volume) was preactivated with oxygen plasma (EUROPLASMA CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% PEG-propionic (Shearwater, 2M3T0P01) ethanol-water solution for 10 minutes. The coated sheet was washed with 100 times water in an ultrasonic bath (VWR) at room temperature for 5 minutes. This washing was repeated three times. The treated sheet was dried at room temperature.

7.20. Example 20

Material Coated with Poly(ethylene Glycol)(Covalent Interaction)

A porous plastic sheet made by Porex Corporation (pore size 7 micron, 35% pore volume) was preactivated with oxygen plasma (EUROPLASMA CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1 % PEG-propionic (Shearwater, 3T3T0F02), 1% Dicylohexylcarbodiimide (DCC) (Sigma, D8000-2) DMF solution for 10 minutes. The coated sheet was washed with 100 times water in an ultrasonic bath (VWR) at room temperature for 5 minutes. This washing was repeated three times. The treated sheet was dried at room temperature.

7.21. Example 21

Material Coated with Anionic Surfactant

A porous plastic sheet made by Porex Corporation (pore size 7 micron, 35% pore volume) was preactivated with oxygen plasma (EUROPLASMA CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% Sodium Dodecylsulfate (Aldrich, 7 1726F) ethanol-water solution for 10 minutes. The coated sheet was washed with 100 times water in an ultrasonic bath (VWR) at room temperature for 5 minutes. This washing was repeated three times. The treated sheet was dried at room temperature.

7.22. Example 22

Material Coated with Cationic Surfactant

A porous plastic sheet made by Porex Corporation (pore size 7 micron, 35% pore volume) was preactivated with oxygen plasma (EUROplasma CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% PAA (Sigma, MW 250,000) ethanol-water solution for 10 minutes. The coated sheet was washed with 100 times water in an ultrasonic bath (VWR) at room temperature for 5 minutes. This washing was repeated three times. The treated sheet was dry at room temperature. Coated porous materials then was immersed into Dodecyltrimethylammonium bromide (DTAB) (Aldrich, (26876-3), ethanol-water solution. The coated sheet was washed with 100 times water in an ultrasonic bath (VWR) at room temperature for 5 minutes. This washing was repeated three times. The treated sheet was dried at room temperature.

7.23. Example 23

Material Coated with Biotin

A porous plastic sheet made by Porex Corporation (pore size 7 micron, 30% pore volume) was pre-activated with oxygen plasma (EUROPLASMA CD600PC), at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% sulfo-NHS-LC-LC-Biotin (Pierce, 21338) ethanol-water solution for 10 minutes. The coated sheet was washed with 100 times water in an ultrasonic bath (VWR) at room temperature for 5 minutes. This washing was repeated three times. The treated sheet was dried at room temperature.

7.24. Example 24

Material Coated with Lipid

A porous plastic sheet made by Porex Corporation (pore size 7 micron, 35% pore volume) was preactivated with oxygen plasma (EUROPLASMA CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 0.1% Fumonisin B 1 (Sigma, F 1147) or L-lysophosphatidic acid (Sigma, L7260) ethanol-water solution for 10 minutes. The coated sheet was washed with 100 times water at room temperature for 5 minutes. This washing was repeated three times. The treated sheet was dried at room temperature.

7.25. Example 25

Material Coated with Nucleic Acids

A porous plastic sheet made by Porex Corporation (pore size 7 micron, 35% pore volume) was preactivated with oxygen plasma (EUROPLASMA CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 0.1% Guanosine 5'-triphosphate sodium salt (Sigma, G8877) ethanol-water solution for 10 minutes. The coated sheet was washed with 100 times water for 5 minutes. This washing was repeated three times. The treated sheet was dried at room temperature.

7.26. Example 26

Material Coated with Protein

A porous plastic sheet made by Porex Corporation (pore size 7 micron, 35% pore volume)-was preactivated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of PAA sodium salt (aldrich, 523925, MW 250,000) ethanol-water solution for 10 minutes. The coated sheet was washed with 100 times water in an ultrasonic bath (VWR) at room temperature for 5 minutes. This washing was repeated three times. The-treated sheet was dried at room temperature. Treated piece was immersed in 0.1% Goat IgG (Sigma, I5256) at room temperature for 2 hours. Then the porous material was rinsed-with deionized water for 1 minute three times. The final product was dried at room temperature.

7.27. Example 27

Hydrophilic Surface for Ceramic Porous Materials

A porous ceramic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of PAA (Aldrich, 523925, MW 250,000) ethanol-water solution for 10 minutes. The coated sheet was washed with 100 times water in an ultrasonic bath (VWR) at room temperature for 5 minutes. This washing was repeated three times. The treated sheet was dried at room temperature.

7.28. Example 28

Hydrophilic Surface for Metal Porous Materials

A porous metal sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of PAA (Aldrich, 523925, MW 250,000) ethanol-water solution for 10 minutes. The coated sheet was washed with 100 times water in an ultrasonic bath (VWR) at room temperature for 5 minutes. This washing was repeated three times. The treated sheet was dried at room temperature.

7.29. Example 29

Oleophobic Ceramic Materials

A porous ceramic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of FSP (DuPont) ethanol-water solution for 10 minutes. The coated sheet was washed with 100 times water in an ultrasonic bath (VWR) at room temperature for 5 minutes. This washing was repeated three times. The treated sheet was dried at room temperature.

7.30. Example 30

Oleophobic Metal Materials

A porous metal sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of FSP (DuPont) ethanol-water solution for 10 minutes. The coated sheet was washed with 100 times water in an ultrasonic bath (VWR) at room temperature for 5 minutes. This washing was repeated three times. The treated sheet was dried at room temperature.

7.31. Example 31

Wicking Characteristics

The hydrophilicity of various porous materials of the invention can be investigated by testing their wicking rate. For example, one end of a test piece (0.5×5 cm strip) is dipped into a 0.5 cm deep testing solution. The time it takes for a particular solution to move up a particular length of the strip (e.g., 4 cm) can be measured. Standard contact angle measurements can be used to determine the hydrophobicity of materials that do not wick.

The wicking rate and stability for PEI/PAA system treated T3 material have been systematically tested. The results show that plasma/PEI/PAA system treated T3 materials have faster wicking rates for the deionized water than oxygen plasma treated plasma/PEI and plasma/PAA treated T3 material. Most important improvement comes from the stability of the wicking rate. T3 materials with only plasma treatment return to hydrophobic during the storage at room or elevated temperature. PEI or PAA individual treatment will improve T3 material wicking stability; however, they still partially decrease the wicking rate under an elevated temperature. PEI/PAA system treated T3 material show very stable wicking rate even under an elevated temperature.

TABLE 4

Wicking rates for different aging porous materials

| Time (Hrs.) | Temperature (° C.) | Plasma | 1% PEI | 1% PEI-0.1% PAA | 0.1% PEI-1% PAA |
|---|---|---|---|---|---|
| 0 | 60 | 38 | 36 | 30 | 40 |
| 3 | 60 | 240 | 60 | 35 | 35 |
| 120 | 60 | no wicking | 54 | 36 | 38 |
| 240 | 60 | no wicking | 62 | 35 | 39 |
| 460 | 60 | no wicking | 60 | 34 | 39 |

Figure 2:
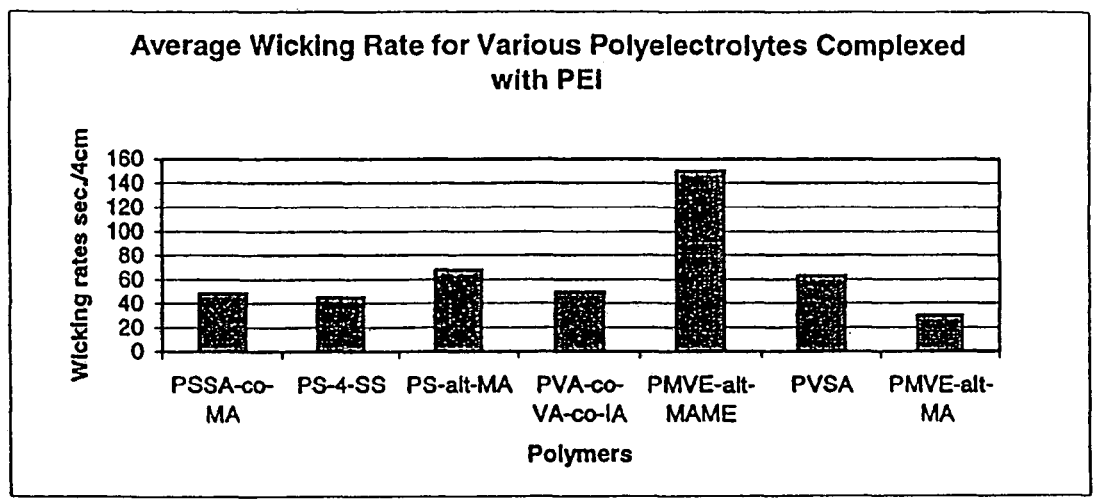
FIG. 2 illustrates the Wicking rates for porous materials treated with different polyelectrolytes.

In addition, FIG. 2 shows the wicking rates, measured in seconds/4 cm, for various polyelectrolytes complexed with PEI. The polyelectrolytes used in FIG. 2 are poly(styrene sulfonic acid-co-maleic acid) (PSSA-co-MA), poly(sodium-4-styrene sulfonate) (PS-4-SS), poly(styrene-alt-maleic acid) (PS-alt-MA), poly(vinyl alcohol-co-vinyl acetate-co-itaconic acid) (PVA-co-VA-co-IA), poly(methyl vinyl ether-alt-maleic acid monoethyl ester) (PMVA-alt-MAME), poly(vinyl sulfonic acid) (PVSA), poly(styrene-co-maleic acid) (PS-co-MA), and poly(methyl vinyl ether-alt-maleic acid) (PMVE-alt-MA).

7.32. Example 32

Resistance to Leaching

Leaching is a common phenomenon for surface modification materials and additives for porous materials. The leaching out of coated molecular will reduce the life time as a filtration device and limit porous materials' application in highly regulated medical device area and highly sensitive chromatography area. The leaching of different molecular can be quantitatively determined using a variety of analytical methods. Examples of the methods that can be used to determine leaching include the following:

(i) Polyelectrolyte: The quantitative amount leach of polyelectrolytes and other molecules can be determined by using UV-VIS and HPLC methods. Polyelectrolytes, such as PEI can form complex with organic dye molecules, such as Bradford reagent. The quantitative of this new complex can be determined using UV-VIS spectrophotometer. The quantitative of polyelectrolytes can be also be determined by Gel Permissive Chromatography (GPC) or Size Exclusive Chromatography (SEC) method.

(ii) Biomolecules: The leach of biomolecules can be determined using HPLC, Mass Spectrometer (MS). It is also possible to determine biomolecule leaching using UV-VIS if the biomolecule can catalyze certain chemical reaction. Such as horseradish peroxidase (HRP) and catalyzed chemical reaction with tetramethyl-benzidine (TMB).

(iii) Small organic molecules and surfactants: The leaching of organic small molecules and surfactants usually can be determined by HPLC, or TV-VIS if there is an adsorption in the UV-VIS range.

(iv) Inorganic ions: UV-VIS, and ICP-MS methods can measure the leaching amount of inorganic ions.

To achieve permanent hydrophilic porous plastics, solid form surfactant is usually applied to the porous plastics. Generally, over 50% of applied surfactant can be washed away from the porous plastic metrics. For example, if a porous plastic have 0.15% surfactant in it, then, 0.075% of surfactant will leach out into the solution, which is the 50% of surfactant.

The amount of leaching out for PEL PEI/PAA, and PAA/PEI complex system can be determined using UV-VIS by reacting with Bradford reagent. This method shows the sensitivity of sub PPM in aqueous solution. Generally, the leaching amount of PEI and PEI/PAA complex depends on the polyelectrolyte solution concentration, washing method, washing solution pH and ionic strength For the PEI and PEI/PAA complex treated T3 porous materials, PEI and PEI/PAA complex leaching is not sensitive to PEI or PAA concentrations if porous materials are washed thoroughly.

TABLE 5

PEI leaching amounts in pure water

| | Sample | | | |
|---|---|---|---|---|
| | PEI (0.1-1%) | PEI/PAA (0.1-1%) | PAA/PEI (0.1-1%) | Surfactant (0.15%) |
| Leaching amount | 80 µg/g | 26 µg/g | 100 µg/g | 750 µg/g |
| Leaching percentage | 0.50% | 0.15% | 0.60% | 50% |

A PEI/PAA sequential treatment can significantly reduce the leaching of PEI. No significant difference was observed among the leaching amount for 1% PEI/1% PAA, 1% PEI/0.1% PAA, 0.1% PEI/1% PAA and 0.1% PEI/0.1% PAA.

Figure 3:
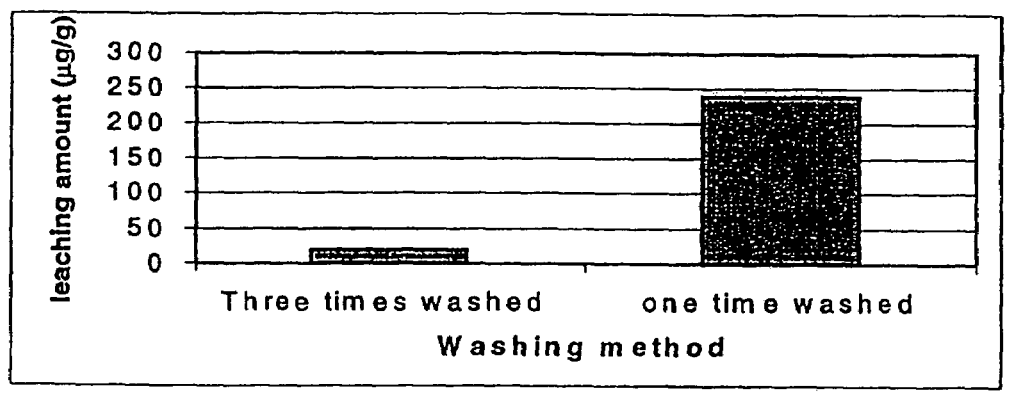
FIG. 3 illustrates the leaching amounts for differently washed PEI/PAA treated porous materials.

PEI/PAA complex leaching also depends on the washing method. A thorough washing step after PEI application and PAA application will significantly reduce the leaching amount. FIG. 3 shows the leaching amounts (micro gram/gram) of two differently washed PEI/PAA treated T3 materials. Sample one was three times vibration washed, Sample 2 was one time non-vibration washed. As demonstrated, Sample 1 showed significant smaller leaching than Sample 2.

Figure 4:
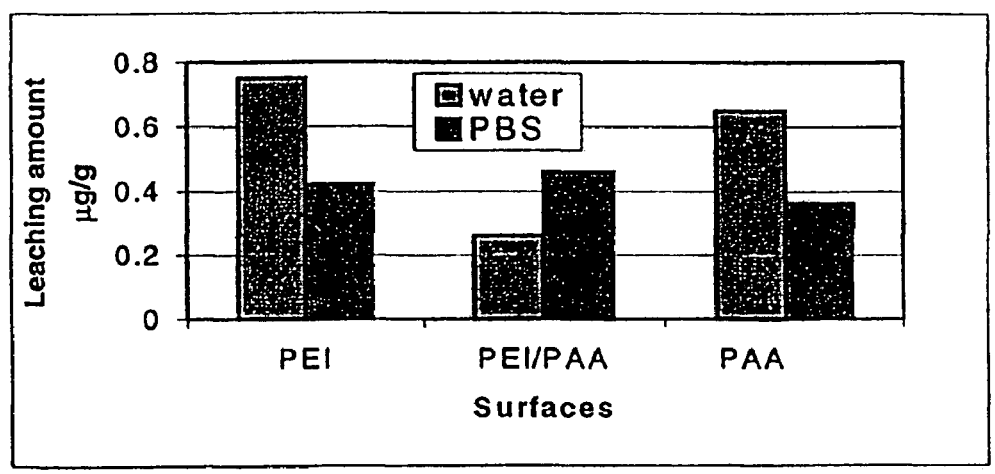
FIG. 4 illustrates the leaching amounts for PEI/PAA treated porous material in PBS and pure water.

PEI/PAA complex has different solubility in different pH and ionic strength. Different surfaces show different leaching out under different washing solution. PEI coated porous plastic shows higher leaching in pure water than in PBS, PEI/PAA complex coated porous plastics shows higher leaching out in PBS and PAA only coated porous plastics shows higher leaching out in pure water. (PBS, 0.01 M, 0.15 M NaCl) (FIG. 4)

PEI/PAA treated T3 material shows much lower leaching in pure water and PBS buffer condition than surfactant treated T3. The overall leaching of PEI is only about 1-2 percent of total immobilized PEI Vs 50% of applied surfactant.

It should be noted that the leaching of PEI/PAA is often undetectable when the amount is less than 0.1 ppm.

7.33. Example 33

Protein Binding

Protein binding was conducted by immersing differently treated porous materials into a protein solution, in which part of proteins have been labeled with enzymes or radioactive isotopes. For enzyme labeled proteins, a chemical substrate reacts with the enzyme and forms a new chemical that has a specific UV absorption band. By measuring the absorption of newly formed chemical substance at a specific wavelength, enzyme activity and amount on the porous materials can be calculated. For the radioactive isotope labeled proteins, the amount of protein on porous material can be measured by measuring the amount of radiation.

Figure 5:
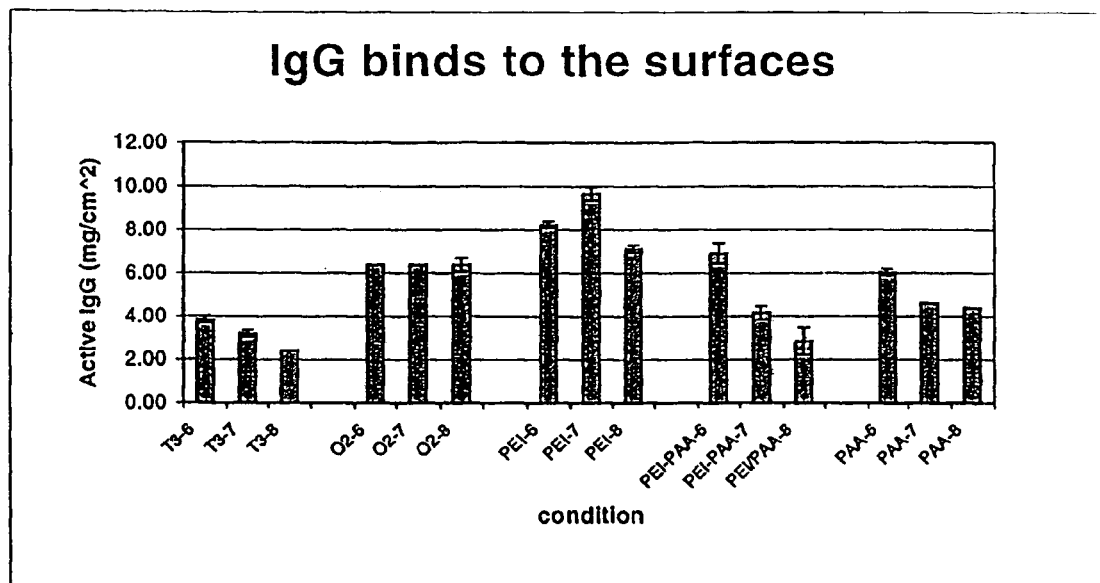
FIG. 5 illustrates IgG binding amounts at different pH for differently treated porous materials (at 0.01 M PBS)

IgG binding amount was tested using enzyme labeled goat anti-rabbit IgG on differently treated T3 porous materials. The results showed that the differently treated T3 material's IgG binding amount under different pH (0.01 M PBS, 0.15 M NaCl) were different. The data indicated that untreated T3 had a decreased IgG binding amount with increase of pH, and-oxygen plasma treated T3 showed no impact of pH on its IgG binding. PEI treated T3 porous material shows the highest IgG binding at pH 7. Both PEI/PAA and PAA treated T3 porous materials showed decreased IgG binding with the increase of pH. PEI/PAA complex treated T3 porous material showed strong pH dependent IgG binding ability, which is a good property for protein extraction and separation. The results are demonstrated in FIG. 5, wherein IgG binding amounts on the surface of untreated (T3), oxygen plasma treated ($O_2$), PEI treated. PEI-PAA treated, and PAA treated T3 material under different pH values (i.e., 6, 7 and 8) are shown.

Figure 6:
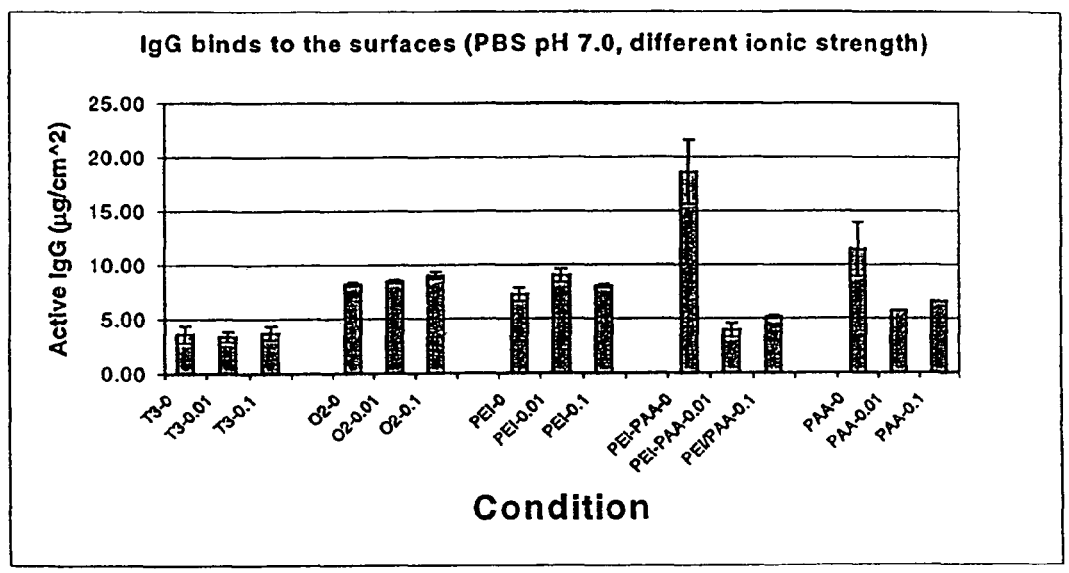
FIG. 6 illustrates IgG binding amount at different ionic strength for differently treated porous materials.

FIG. 6 shows the differently treated T3 porous material's IgG binding ability (pH 7) under different ionic strength (deionized water, 0.01 M PBS buffer, 0.1 M PBS buffer, which translate into 0, 0.15, and 1.5 ionic strength, respectively). The data indicate that untreated T3 porous material and oxygen plasma treated T3 porous material do not have ionic strength dependent IgG binding. PEI treated T3 porous material had the highest IgG binding at ionic strength of 0.15. Both PEI/PAA and PAA treated T3 materials showed significant decrease of IgG binding from ionic strength 0 to ionic strength of 0.15. However, there was little difference between ionic strength of 0.15 and 1.5. PEI/PAA complex treated T3 porous material showed ionic strength dependent IgG binding ability, which is a good property for protein extraction and separation.

Figure 7:
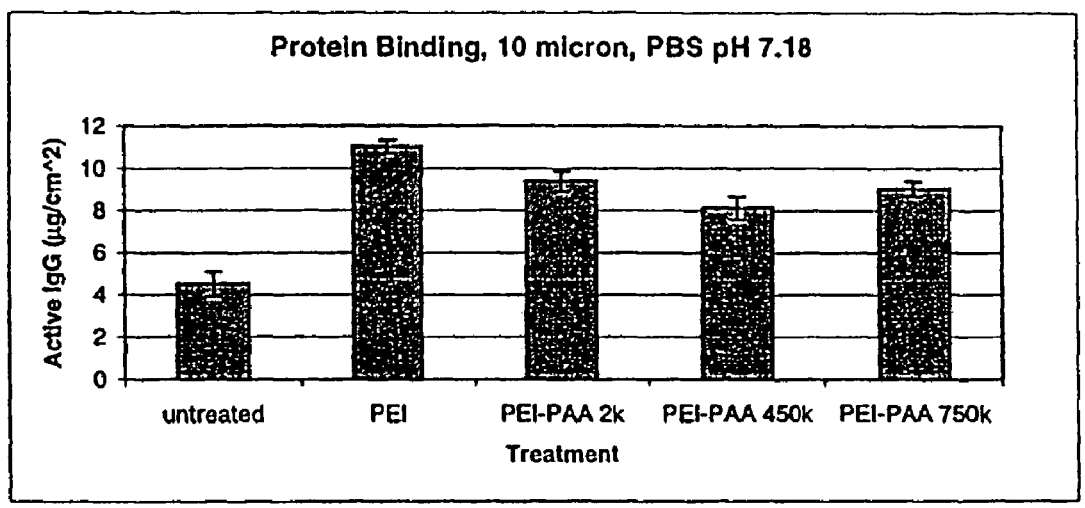
FIG. 7 illustrates IgG binding amounts on various PEI/PAA treated porous materials.

FIG. 7 shows the results of protein (IgG) binding to differently treated materials. The materials have an average pore size of 10 micro meters and the binding assays were conducted at appH value of 7.18.

Figure 8:
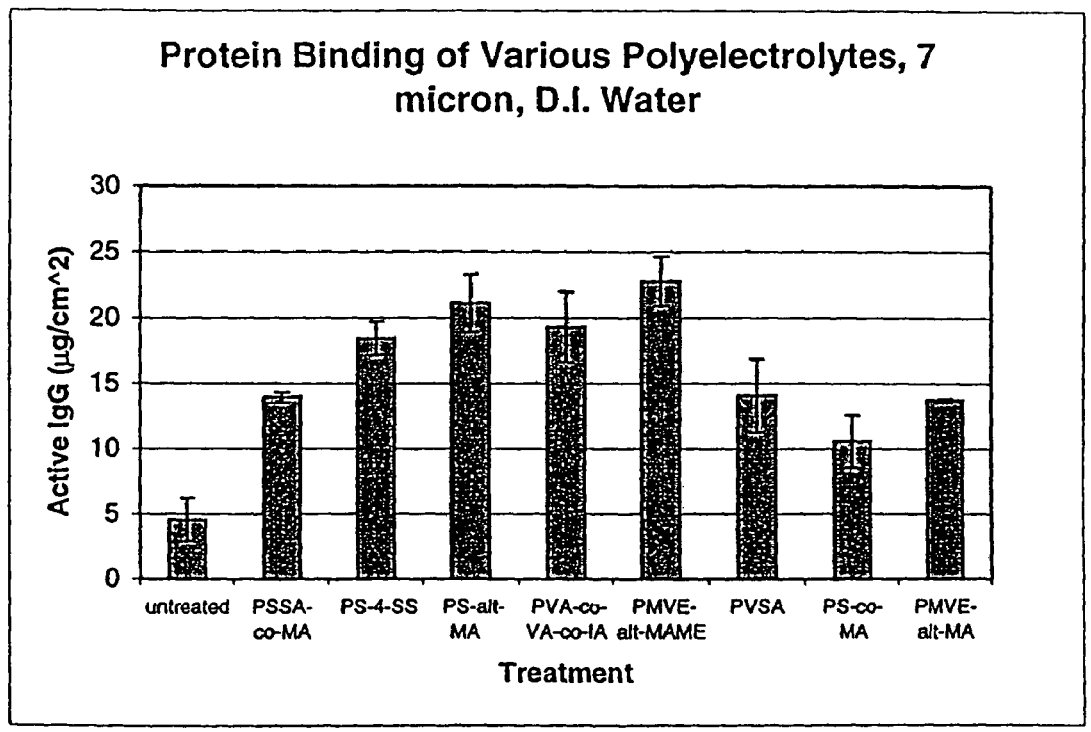
FIG. 8 illustrates IgG binding amounts on porous materials treated with different polyelectrolytes.

FIG. 8 shows the results of protein (IgG) binding to materials treated with different polyelectrolytes. The materials have an average pore size of 7 micro meters and the binding assays were conducted under a pH value of 7.

As those skilled in the art will readily recognize, this invention is not limited to the details provided above or shown in the attached figures. Instead, the invention is best understood with reference to the following claims.

What is claimed is:

1. A multi-layer coated material comprising a surface activated substrate, a first layer, and a second layer, wherein the surface activated substrate comprises a sintered porous polymeric material; the first layer comprises polyethylenimine molecules bound directly to a surface of the surface activated substrate through covalent bonds and electrostatic interactions, the polyethylenimine molecules comprising neutral amine functional groups and charged amine functional groups; and the second layer comprises polyelectrolyte molecules bound to the first layer through covalent bonds, electrostatic interactions, or combinations thereof.

2. The material of claim 1, wherein the polymeric material comprises a polyolefin, polyester, polyurethane, polycarbonate, polyetheretherketone, poly(phenylene oxide), poly(ether sulfone), or nylon.

3. The material of claim 2, wherein the polyolefin comprises ethylene vinyl acetate, ethylene methyl acrylate, polyethylene, polypropylene, ethylene-propylene rubber, ethylene-propylene-diene rubbers, poly(1-butene), polystyrene, poly(2-butene), poly(1-pentene), poly(2-pentene), poly(3-methyl-1-pentene), poly(4-methyl-1-pentene), 1,2-poly-1,3-butadiene, 1,4-poly-1,3-butadiene; polyisoprene, polychloroprene, poly(vinyl acetate), poly(vinylidene chloride), poly(vinylidene fluoride), poly(tetrafluoroethylene), or mixtures thereof.

4. The material of claim 1, wherein the polyelectrolyte molecules of the second layer comprise poly(acrylic acid), a copolymer containing poly(acrylic acid), or a surfactant.

5. The material of claim 4, wherein the polyelectrolyte molecules of the second layer comprise a fluorinated surfactant.

6. The material of claim 1 further comprising at least one additional layer of polyelectrolyte molecules bound to the second layer through covalent bonds, electrostatic interactions, or combinations thereof.

7. The material of claim 6, wherein the polyelectrolyte molecules of the second layer comprise poly(acrylic acid) or a copolymer containing poly(acrylic acid), and the polyelectrolyte molecules of the at least one additional layer comprise polyethylenimine.

8. A multi-layer coated material comprising a surface activated substrate, a first layer, and a second layer, wherein the surface activated substrate comprises a sintered porous polymeric material; the first layer comprises polyethylenimine molecules bound directly to a surface of the surface activated substrate through covalent bonds and electrostatic interactions, the polyethylenimine molecules comprising neutral amine functional groups and charged amine functional groups; and the second layer comprises poly(acrylic acid) molecules bound to the first layer through covalent bonds, electrostatic interactions, or combinations thereof.

9. A multi-layer coated material comprising a surface activated substrate, a first layer, and a second layer, wherein the surface activated substrate comprises a sintered porous polymeric material; the first layer comprises polyethylenimine molecules bound directly to a surface of the surface activated substrate through covalent bonds and electrostatic interactions, the polyethylenimine molecules comprising neutral amine functional groups and charged amine functional groups; and the second layer comprises poly(acrylic acid) molecules bound directly to the first layer through covalent bonds and electrostatic interactions, the poly(acrylic acid) molecules comprising neutral carboxyl functional groups and charged carboxyl functional groups.

* * * * *